(12) United States Patent
Hoskuldsson et al.

(10) Patent No.: US 10,548,497 B2
(45) Date of Patent: Feb. 4, 2020

(54) SYSTEMS AND METHODS USING FLEXIBLE CAPACITIVE ELECTRODES FOR MEASURING BIOSIGNALS

(71) Applicant: NOX MEDICAL, Reykjavik (IS)

(72) Inventors: Sveinbjorn Hoskuldsson, Reykjavik (IS); Bjorgvin Gudmundsson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 999 days.

(21) Appl. No.: 14/949,344

(22) Filed: Nov. 23, 2015

(65) Prior Publication Data
US 2016/0073921 A1 Mar. 17, 2016

Related U.S. Application Data

(63) Continuation of application No. 13/320,564, filed as application No. PCT/IS2010/000007 on May 17, 2010, now Pat. No. 9,192,316.

(30) Foreign Application Priority Data

May 15, 2009 (DK) .................................. 2009 00624

(51) Int. Cl.
*A61B 5/0402* (2006.01)
*A61B 5/0408* (2006.01)
(Continued)

(52) U.S. Cl.
CPC ........ *A61B 5/04085* (2013.01); *A61B 5/0408* (2013.01); *A61B 5/0478* (2013.01);
(Continued)

(58) Field of Classification Search
CPC . A61B 5/1135; A61B 5/0408; A61B 5/04085; A61B 5/04285; A61B 5/0478;
(Continued)

(56) References Cited

U.S. PATENT DOCUMENTS

| 937,130 A | 10/1909 | Williams |
| 1,001,054 A | 8/1911 | Lawrence |

(Continued)

FOREIGN PATENT DOCUMENTS

| DE | 199 41 500 A1 | 3/2001 |
| DE | 19941500 A1 | 3/2001 |

(Continued)

OTHER PUBLICATIONS

International Search Report from PCT Application No. PCT/IS2011/050010, dated Feb. 29, 2012.

(Continued)

*Primary Examiner* — Lee S Cohen
*Assistant Examiner* — Erin M Cardinal
(74) *Attorney, Agent, or Firm* — Workman Nydegger

(57) ABSTRACT

A system and method are provided for measuring biometric signals. The system includes a first electrode, a second electrode and a circuit. The first electrode forms at least a portion of a first belt configured to be placed at least partially around a torso of a subject. The second electrode forms at least a portion of a second belt configured to be placed at least partially around the torso. The circuit is configured to measure a voltage between the first electrode and the second electrode. The first and second electrodes are arranged to determine the respiratory effort of the subject. The first or second electrode includes a capacitive electrode with a flexible structure including an insulated conductor. The insulated conductor is insulated such that the conductor does not come in direct contact with skin of the subject when the first or second electrode is placed on the subject.

18 Claims, 5 Drawing Sheets

(51) Int. Cl.
  *A61B 5/0488*  (2006.01)
  *A61B 5/0492*  (2006.01)
  *A61B 5/08*    (2006.01)
  *A61B 5/0428*  (2006.01)
  *A61B 5/0478*  (2006.01)
  *A61B 5/113*   (2006.01)
  *A61B 5/00*    (2006.01)

(52) U.S. Cl.
  CPC ........ *A61B 5/0492* (2013.01); *A61B 5/04284* (2013.01); *A61B 5/0809* (2013.01); *A61B 5/1135* (2013.01); *A61B 5/6804* (2013.01); *A61B 5/6805* (2013.01); *A61B 5/6823* (2013.01); *A61B 5/6831* (2013.01); *A61B 5/4806* (2013.01); *A61B 5/721* (2013.01)

(58) Field of Classification Search
  CPC ... A61B 5/0492; A61B 5/0809; A61B 5/4806; A61B 5/6804; A61B 5/6805; A61B 5/6831; A61B 5/04284; A61B 5/04004; A61B 5/0488
  See application file for complete search history.

(56) References Cited

U.S. PATENT DOCUMENTS

| | | | |
|---|---|---|---|
| 1,115,459 A | 10/1914 | Abizaid | |
| 1,193,050 A | 8/1916 | Orewiler | |
| 2,305,277 A | 12/1942 | Sloane et al. | |
| 2,649,573 A | 8/1953 | Goldberg et al. | |
| 2,667,159 A | 1/1954 | Goldberg et al. | |
| 3,092,759 A | 6/1963 | Sommer | |
| 3,347,223 A | 10/1967 | Pacela | |
| 3,500,823 A | 3/1970 | Richardson et al. | |
| 3,560,845 A | 2/1971 | Goldber et al. | |
| 3,685,105 A | 8/1972 | Carlile et al. | |
| 4,308,872 A | 1/1982 | Watson et al. | |
| 4,373,534 A | 2/1983 | Watson | |
| 4,430,777 A | 2/1984 | Takeda | |
| 4,671,591 A | 6/1987 | Archer | |
| 4,777,962 A | 10/1988 | Watson et al. | |
| 4,807,640 A | 2/1989 | Watson et al. | |
| 4,815,473 A | 3/1989 | Watson et al. | |
| 4,817,625 A | 4/1989 | Miles | |
| 4,832,608 A | 5/1989 | Kroll | |
| 4,834,109 A | 5/1989 | Watson | |
| 4,842,557 A | 6/1989 | Muz | |
| 4,895,162 A * | 1/1990 | Dolliver | A61B 5/04085 600/534 |
| 5,301,678 A | 4/1994 | Watson et al. | |
| 5,326,272 A | 7/1994 | Harhen et al. | |
| 5,331,968 A * | 7/1994 | Williams | A61B 5/0809 600/534 |
| 5,348,008 A * | 9/1994 | Bornn | A61B 5/0006 600/301 |
| 5,353,793 A | 10/1994 | Bornn | |
| 5,543,012 A | 8/1996 | Watson et al. | |
| 6,148,486 A | 11/2000 | Uehara et al. | |
| 6,327,486 B1 * | 12/2001 | Nissila | A61B 5/02438 128/903 |
| 6,341,504 B1 | 1/2002 | Istook | |
| 6,413,225 B1 | 6/2002 | Sackner et al. | |
| 6,461,307 B1 | 10/2002 | Kristbjarnarson et al. | |
| 6,807,438 B1 * | 10/2004 | Brun Del Re | A61B 5/04004 128/902 |
| 6,993,378 B2 | 1/2006 | Wiederhold et al. | |
| 7,171,265 B2 | 1/2007 | Hoium et al. | |
| 7,267,652 B2 | 9/2007 | Coyle et al. | |
| 7,593,767 B1 | 9/2009 | Modarres | |
| 7,604,603 B2 | 10/2009 | Sackner et al. | |
| 7,670,295 B2 | 3/2010 | Sackner et al. | |
| 7,727,161 B2 | 6/2010 | Coyle et al. | |
| 7,762,953 B2 | 7/2010 | Derchak et al. | |
| 7,819,710 B2 | 10/2010 | McIntire et al. | |
| 7,878,979 B2 | 2/2011 | Derchak | |
| 7,914,350 B1 | 3/2011 | Bozich et al. | |
| 8,025,539 B2 | 9/2011 | Hermannsson | |
| 8,033,996 B2 | 10/2011 | Behar | |
| 8,034,001 B2 | 10/2011 | Gal | |
| 8,052,612 B2 | 11/2011 | Tang et al. | |
| 8,137,270 B2 | 3/2012 | Keenan et al. | |
| 8,165,654 B2 | 4/2012 | Tang et al. | |
| 8,177,724 B2 | 5/2012 | Derchak et al. | |
| 8,193,821 B2 | 6/2012 | Mueller et al. | |
| 8,251,736 B2 | 8/2012 | McIntire et al. | |
| 8,475,387 B2 | 7/2013 | Derchak et al. | |
| 8,579,794 B2 | 11/2013 | Henke | |
| 8,628,480 B2 | 1/2014 | Derchak | |
| 8,679,012 B1 | 3/2014 | Kayyali | |
| 8,762,733 B2 | 6/2014 | Derchak et al. | |
| 8,777,868 B2 | 7/2014 | Gal | |
| 8,790,255 B2 | 7/2014 | Behar | |
| 8,790,272 B2 | 7/2014 | Sackner et al. | |
| 9,059,532 B2 | 6/2015 | Hermannsson | |
| 2002/0032386 A1 * | 3/2002 | Sackner | A61B 5/0205 600/536 |
| 2002/0032388 A1 | 3/2002 | Kristbjarnarson et al. | |
| 2002/0120207 A1 | 8/2002 | Hoffman | |
| 2003/0135127 A1 | 7/2003 | Sackner et al. | |
| 2005/0054941 A1 | 3/2005 | Ting et al. | |
| 2005/0119586 A1 * | 6/2005 | Coyle | A61B 5/0806 600/538 |
| 2006/0122528 A1 * | 6/2006 | Gal | A61B 5/1135 600/534 |
| 2006/0258948 A1 | 11/2006 | Linville | |
| 2006/0282001 A1 * | 12/2006 | Noel | A61B 5/0816 600/535 |
| 2007/0167089 A1 | 7/2007 | Gobron et al. | |
| 2009/0259135 A1 * | 10/2009 | Stasz | A61B 5/1135 600/534 |
| 2010/0060300 A1 | 3/2010 | Muller et al. | |
| 2010/0075527 A1 | 3/2010 | McIntire et al. | |
| 2010/0075549 A1 | 3/2010 | McIntire et al. | |
| 2010/0297868 A1 | 11/2010 | Hermannsson | |
| 2011/0151728 A1 | 6/2011 | Astola | |
| 2011/0248729 A2 | 10/2011 | Mueller et al. | |
| 2012/0035435 A1 * | 2/2012 | Choi | A61B 5/04085 600/301 |
| 2012/0101357 A1 | 4/2012 | Hoskuldsson et al. | |
| 2014/0323847 A1 | 10/2014 | McCool | |
| 2015/0126879 A1 * | 5/2015 | Hoskuldsson | A61B 5/0806 600/484 |
| 2015/0280348 A1 | 10/2015 | Hermannsson | |
| 2016/0135715 A1 | 5/2016 | Seppä et al. | |
| 2017/0110823 A1 | 4/2017 | Hermannsson et al. | |
| 2017/0143206 A1 | 5/2017 | Kotz et al. | |
| 2018/0049678 A1 * | 2/2018 | Hoskuldsson | A61B 5/087 |

FOREIGN PATENT DOCUMENTS

| | | | |
|---|---|---|---|
| EP | 2324760 A2 | 5/2011 | |
| EP | 2324761 A2 | 5/2011 | |
| EP | 2417905 A1 | 2/2012 | |
| EP | 2484276 A2 | 8/2012 | |
| EP | 2484277 A2 | 8/2012 | |
| EP | 2484278 A3 | 8/2012 | |
| EP | 2508123 A2 | 10/2012 | |
| EP | 2508124 A2 | 10/2012 | |
| EP | 2584962 A2 | 5/2013 | |
| EP | 2589335 A2 | 5/2013 | |
| WO | 02/02013 A1 | 1/2002 | |
| WO | 02/080761 A2 | 10/2002 | |
| WO | 2006024024 A2 | 3/2006 | |
| WO | 2006/066566 A2 | 6/2006 | |
| WO | 2008102140 A1 | 8/2008 | |
| WO | D071077-002 | 10/2008 | |
| WO | 20080133394 A1 | 11/2008 | |

(56) References Cited

FOREIGN PATENT DOCUMENTS

| WO | 2011029136 A1 | 3/2011 |
|---|---|---|
| WO | 2018033889 A1 | 2/2018 |

OTHER PUBLICATIONS

International Search Report from PCT Application No. PCT/IB2014/002760, dated Mar. 27, 2015.
International Preliminary Report on Patentability from PCT Application No. PCT/IB2014/002760, dated May 10, 2016.
"Opinion Regarding European Patent, 2584962", Kilbun & Strode, dated Mar. 11, 2015, 14 Pages.
Notice of Appeal, Western High Court, Cephalon A/S, VS, Nox Medical Ehf, Mar. 9, 2015, 10 Pages.
"Defendant's Preliminary Invalidity and Unenforceability Contentions," Nox Medical EHF v. Natus Neurology Inc., Defendants, Civil Action No. 1:15-cv-00709-RGA, In the United States District Court for the District of Delaware, Apr. 15, 2016, 117 Pages.
"Defendant's First Supplemental Invalidity and Unenforceability Contentions," Nox Medical EHF v. Natus Neurology Inc., Defendants, Civil Action No. 1:15-cv-00709-RGA, In the United States District Court for the District of Delaware, Dec. 1, 2016, 3 Pages.
"Defendant's Second Supplemental Invalidity and Unenforceability Contentions," Nox Medical EHF v. Natus Neurology Inc., Defendants, Civil Action No. 1:15-cv-00709-RGA, In the United States District Court for the District of Delaware, 2009, 59 Pages.
"Defendant's Third Supplemental Invalidity and Unenforceability Contentions," Nox Medical EHF v. Natus Neurology Inc., Civil Action No. 1:15-cv-00709-RGA, In the United States District Court for the District of Delaware, Feb. 17, 2017, 4 Pages.
Patent Owner's Preliminary Response to U.S. Pat. No. 9,059,532, Dec. 27, 2016. 86 Pages.
Response to Opposition for European Patent No. 2584962, Nov. 23, 2015, 154 Pages.
"Disposable and Accessories Catalog for Respiratory Diagnostics", CareFusion, Natus Medical Inc., 2009, 138 Pages.
Petition for Inter Partes Review of U.S. Pat. No. 9,059,532, Sep. 15, 2016.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
Cohen, Kevin P. et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.
Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.
Stromberg, N.O.T., "Error analysis of a natural breathing calibration method for respiratory inductive plethysmography", Medical & Biological Engineering & Computing 2001, vol. 39, No. 3, May 1, 2001, pp. 310-314.
International Search Report from International PCT Application No. PCT/IS2010/000007, dated Oct. 1, 2010.
International Search Report from International PCT Application No. PCT/IB2014/002760, dated Mar. 27, 2015.
International Search Report from PCT Application No. PCT/IB2017/053128, dated Aug. 9, 2017.
Minutes of OP and Interlocutory Decision from Application No. 11 758 266.8, Nov. 6, 2017.
Notification of Minutes and Amendments at OP from Application No. 11 758 266.8, Nov. 6, 2017.
OP Decision and Reasoning from Application No. 11 758 266.8, Nov. 6, 2017.
Opposition against EP Application No. 11758266.8, Dec. 16, 2015.
Letter containing Test Results from European U.S. Pat. No. 2,584,962, dated Feb. 23, 2017.
Escobar et al., "Nu-Way Snaps and Snap Leads: an Important Connection in the History of Behavior Analysis," Behav Analyst, 2014, vol. 37, pp. 95-107.
Declaration of Mr. Ami Vilhjalmsson, Apr. 11, 2017, 3 Pages.
Declaration of Mr. Hilmarsson, Apr. 6, 2017, 1 Page.
Declaration of Ms. Erna Sif Amardottir, 1 Page, Apr. 21, 2017.
Agustsson et al., "White Paper RIP Signal Assessment," Apr. 21, 2017, 21 Pages.
Statement of Mr. Sveinbjorn Hoskuldsson, Apr. 24, 2017, 2 Pages.
Statement from Mr. Andres Einar Hilmarsson, Apr. 24, 2017, 1 Page.
Declaration of Ms. Erla S. Amadottir, Apr. 25, 2017. 5 Pages.
Attachment A, to Natus' Third Supplemental Invalidity and Unenforceability Contentions, U.S. Pat. No. 9,059,532, Nox Medical Ehf. v. Natus Neurology, Inc., Civil Action No. 15-cv-00709-RGA (D. Del), 63 Pages.
Agha et al., "Facial Phenotype in Obstructive Sleep Apnea—Hypopnea Syndrome: A Systematic Review and Meta-Analysis," Journal of Sleep Research, vol. 26, 2017, pp. 122-131.
Agrawal et al., "Sound Frequency Analysis and the Site of Snoring in Natural and Induced Sleep," Clinical Otolaryngology, vol. 27, 2002, pp. 162-166.
Akoumianaki et al., "The Application of Esophageal Pressure Measurement in Patients with Respiratory Failure," American Journal of Respiratory and Critical Care Medicine, vol. 189, No. 5, Mar. 1, 2014, pp. 520-531.
Arnardottir et al., "Snoring—Validation of Different Objective Measurements," European Respiratory Society Annual Congress 2013, 1 Page.
Arnardottir et al., "How to Measure Snoring? A Comparison of the Microphone, Cannula and Piezoelectric Sensor," Journal of Sleep Research, vol. 25, 2016, pp. 158-168.
Arnardottir et al., "Obstructive Sleep Apnoea in the General Population: Highly Prevalent but Minimal Symptoms," European Respiratory Journal, vol. 47, 2016, pp. 194-202.
Ayappa et al., "Non-Invasive Detection of Respiratory Effort-Related Arousals (RERAs) by a Nasal Cannula/Pressure Transducer System," Sleep, vol. 23, No. 6, 2000, pp. 763-771.
Berry et al., "Use of Chest Wall Electromyography to Detect Respiratory Effort During Polysomnography," Journal of Clinical Sleep Medicine, vol. 12, No. 9, 2016, pp. 1239-1244.
Berry et al., "AASM Scoring Manual Updates for 2017 (Version 2.4)," Journal of Clinical Sleep Medicine, vol. 13, No. 5, 2017, pp. 665-666.
Bloch et al., "Breathing Pattern During Sleep Disruptive Snoring," European Respiratory Journal, vol. 10, 1997, pp. 576-586.
Capistrano et al., "Facial Morphology and Obstructive Sleep Apnea," Dental Press Journal of Orthodontics, vol. 20, No. 6, Nov. 2015, pp. 60-67.
Eckert et al., "Pathophysiology of Adult Obstructive Sleep Apnea," Proceedings of the American Thoracic Society, vol. 5, 2008, pp. 144-153.
Faber et al., "Available Techniques for Objective Assessment of Upper Airway Narrowing in Snoring and Sleep Apnea," Sleep and Breathing, vol. 7, No. 2, 2003, pp. 77-86.
Ghafarian et al., "A Review on Human Respiratory Modeling," Tanaffos, vol. 15, No. 2, 2016, pp. 61-69.
Guilleminault et al., "Variability of Respiratory Effort in Relation to Sleep Stages in Normal Controls and Upper Airway Resistance Syndrome Patients," Sleep Medicine, vol. 2, 2001, pp. 397-406.
Harris et al., "GPCR Signalling in Hypertension: Role of GRKs," Clinical Science, vol. 115, 2008, pp. 79-89.
Heinzer et al., "Prevalence of Sleep-Disordered Breathing in the General Population: the HypnoLaus Study," Lancet Respiratory Medicine, vol. 3, No. 4, Apr. 2015, pp. 310-318.
Huo et al., "Endoscopic Upper Airway Evaluation in Obstructive Sleep Apnea: Mueller's Maneuver Versus Simulation of Snoring," Sleep Breath, vol. 19, 2015, pp. 661-667.
Konno et al., "Measurement of the Separate Volume," Journal of Applied Physiology, vol. 22, No. 3, 1967, pp. 407-422.

(56) References Cited

OTHER PUBLICATIONS

Kushida et al., "Technical Protocol for the use of Esophageal Manometry in the Diagnosis of Sleep-Related Breathing Disorders," Sleep Medicine, vol. 3, 2002, pp. 163-173.
Lee et al., "Energy Types of Snoring Sounds in Patients with Obstructive Sleep Apnea Syndrome: A Preliminary Observation," PLOS ONE, vol. 7, No. 12, Dec. 2012, 11 Pages.
Luo et al., "Diaphragm Electromyography Using an Oesophageal Catheter: Current Concepts," Clinical Science, vol. 115, 2008, pp. 233-244.
Masa et al., "Apnoeic and Obstructive Nonapnoeic Sleep Respiratory Events," European Respiratory Journal, vol. 34, 2009, pp. 156-161.
Otis et al., "Mechanical Factors in Distribution of Pulmonary Ventilation," Journal of Applied Physiology, vol. 8, No. 4, Jan. 1956, pp. 427-443.
Peppard et al., "Increased Prevalence of Sleep-Disordered Breathing in Adults," American Journal of Epidemiology, vol. 177, No. 9, Apr. 14, 2013, pp. 1006-1014.
Spinowitz et al., "Patterns of Upper Airway Obstruction on Drug-Induced Sleep Endoscopy in Patients with Sleep-Disordered Breathing with AHI < 5," American Academy of Otolaryngology—Head and Neck Surgery, 2017, 6 Pages.
Terrill et al., "Quantifying the Ventilatory Control Contribution to Sleep Apnoea Using Polysomnography," European Respiratory Journal, vol. 45, 2015, pp. 408-418.
Vandenbussche et al., "Assessment of Respiratory Effort During Sleep: Esophageal Pressure Versus Noninvasive Monitoring Techniques," Sleep Medicine Reviews, vol. 24, 2015, pp. 28-36.
Wellman et al., "A Method for Measuring and Modeling the Physiological Traits Causing Obstructive Sleep Apnea," Journal of Applied Physiology, vol. 110, 2011, pp. 1627-1637.
Wilson, "Compartmental Models of the Chest Wall and the Origin of Hoover's Sign," Respiratory Physiology & Neurobiology, vol. 210, 2015, pp. 23-29.
Duarte, "Detect Peaks in Data Based on Their Amplitude and Other Features.," retrieved from https://github.com/demotu/BMC/blob/master/functions/detect_peaks.py on Jun. 1, 2018, Oct. 3, 2014, 3 Pages.
Jones et al., "SciPy: Open Source Scientific Tools for Python," requested from http://www.scipy.org on Jun. 4, 2018, 2001, 3 Pages.
Orphanidou et al., "Signal-Quality Indices for the Electrocardiogram and Photoplethysmogram: Derivation and Applications to Wireless Monitoring," IEEE Journal of Biomedical and Health Informatics, vol. 19, No. 3, May 2015, pp. 832-838.
Roebuck et al., "A Review of Signals Used in Sleep Analysis," Physiological Measurement, vol. 35, 2014, pp. R1-R57.
International Search Report from PCT Application No. PCT/IB2018/053993, dated Aug. 24, 2018.
Lester et al., ""Are You With Me?"—Using Accelerometers to Determine if Two Devices are Carried by the Same Person," Pervasive, 2004, pp. 33-50.
Nino et al., "Robust Spectral Analysis of Thoraco-Abdominal Motion and Oxymetry in Obstructive Sleep Apnea," 35th Annual International Conference of the IEEE EMBS, Jul. 3, 2013, pp. 2906-2910.
De Groote et al., "Mathematical Assessment of Qualitative Diagnostic Calibration for Respiratory Inductive Plethysmorgraphy," Journal of Applied Physiology, vol. 90, 2001, pp. 1025-1030.
Konno et al., "Measurement of the Separate vol. Changes of Rib Cage and Abdomen During Breathing," Journal of Applied Physiology, vol. 22, No. 3, 1967, pp. 407-422.
Sackner et al., "Calibration of Respiratory Inductive Plethysmograph During Natural Breathing," Journal of Applied Physiology, vol. 66, No. 1, 1989, pp. 410-420.
"Defendant's Fourth Supplemental Invalidity and Unenforceability Contentions," *Nox Medical ehf v. Natus Neurology Inc.*, Civil Action No. 1:15-cv-00709-RGA, Mar. 22, 2017, 214 Pages.
"Natus Neurology Inc.'s Combined (1) Reply Brief in Support of Its Motion for Summary Judgment of Invalidity, (2) Brief in Opposition to Nox's Cross-Motion for Summary Judgment of No Invalidity, and (3) Brief in Opposition to Nox's Proposed Claim Constructions," *Nox Medical ehf v. Natus Neurology Inc.*, Civil Action No. 1:15-cv-00709-RGA, Aug. 15, 2017, 416 Pages.
Statement Setting out the Grounds of Appeal from EP Application No. 11758266.8, Mar. 22, 2018, 62 Pages.
Final Written Decision, Inter Partes Review, *Natus Medical Inc., Natus Neurology Inc., Embla Systems LLC, and Embla Systems LTD.*, Petitioner, v. *Nox Medical ehf* for U.S No. 9,059,532, Mar. 21, 2018, 39 Pages.
Patent Owner's Response Under 37 C.F.R 42.120, for U.S. Pat. No. 9,059,532, Jun. 29, 2017, 238 Pages.
Petitioners' Reply Pursuant to 37 C.F.R 42.23 (Redacted—Public Version), for U.S. Pat. No. 9,059,532, Oct. 9, 2017, 38 Pages.
Memorandum Opinion from Civil Action No. 15-709-RGA, *Nox Medical ehf v. Natus Neurology Inc.*, Feb. 13, 2018, 24 Pages.
Judgment from Civil Action No. 15-709-RGA, *Nox Medical ehf v. Natus Neurology Inc.*, May 8, 2018, 1 Page.
Plaintiff Nox Medical's Combined (1) Brief in Opposition to Natus' Motion for Summary Judgment of Invalidity, (2) Opening Brief in Support of Nox Medical's Cross-Motion for Summary Judgment of No Invalidity, and (3) Opening Brief in Support of Nox Medical's Proposed Claim Constructions from Civil Action No. 15-709-RGA, *Nox Medical ehf v. Natus Neurology Inc.*, Jul. 26, 2017, 63 Pages.
Plaintiff Nox Medical EHF's Reply Brief in Further Support of Its Cross-Motion for Summary Judgment of No Invalidity from Civil Action No. 15-709-RGA, *Nox Medical ehf v. Natus Neurology Inc.*, Aug. 23, 2017, 18 Pages.
Order from Civil Action No. 15-709-RGA, *Nox Medical ehf v. Natus Neurology Inc.*, Feb. 13, 2018, 1 Page.
Verdict Form from Civil Action No. 15-709-RGA, *Nox Medical ehf v. Natus Neurology Inc.*, May 7, 2018, 2 Pages.
Natus Neurology Inc.'s Brief in Support of Summary Judgment of Invalidity of the Asserted Claims of U.S. Pat. No. 9,059,532 from Civil Action No. 1:15-709-RGA, *Nox Medical ehf v. Natus Neurology Inc.*, Jul. 7, 2017, 24 Pages.
Augousti et al., "Comparative Analysis of the Isovolume Calibration Method for Non-Invasive Respiratory Monitoring Techniques Based on Area Transduction Versus Circumference Transduction Using the Connected Cylinders Model," Physiological Measurement, vol. 32, 2011, pp. 1265-1274.
International Search Report and Written Opinion from PCT Application No. PCT/IB2018/056892, dated Dec. 13, 2018.

* cited by examiner

SYSTEMS AND METHODS USING FLEXIBLE CAPACITIVE ELECTRODES FOR MEASURING BIOSIGNALS

CROSS-REFERENCE TO RELATED APPLICATIONS

This application is a continuation of U.S. patent application Ser. No. 13/320,564, now U.S. Pat. No. 9,192,316, which is a national stage entry of PCT/IS2010/000007, the entire contents of which are herein incorporated by reference.

FIELD OF THE DISCLOSURE

The present disclosure relates to the field biometric systems for electronic measurements of biosignals, including electrocardiography signals and breathing measurements.

TECHNICAL BACKGROUND

Electrophysiological signals from human or animal bodies are some of the most fundamental signals used in medical diagnostics. Such signals originate from the muscular, cardiac or neurological electronic activity of a living body.

For recording of heart, muscular or neurological electric activities (including the methods of Electrocardiography (ECG), Electromyography (EMG), Electroencephalography (EEG) and Electrooculography (EOG)) skin-electrodes are normally glued to the skin of the patient. The measured signal is based on the potential between the electrodes, which is dependent on the sum of the neural and muscular electronic activity between the electrodes. The quality of the signal is greatly affected by the accuracy of the position of the electrode and the conductance of the skin. For this reason the surface-skin must be scrubbed off and various fluids or gels are used, to get the electrode in direct galvanic contact with the internal body fluids. This makes the use of electrodes semi-invasive and makes it difficult for other than health-professionals to perform the setup. This can often be a problem, e.g. for sleep research and diagnosis, where overnight measurements are needed.

Sleep Studies

To get accurate results from a sleep study, the patient must feel comfortable and sleep normally. Studies have shown that there is a significant difference between the results from the first night measured and the following nights, when the patient is more comfortable with the studies. Optimally the patient should therefore be measured for two or more nights.

When a full sleep diagnostic study (polysomnography, PSG) is performed, a combination of parameters are measured, including the above mentioned electrophysiological parameters along with large number of other sensor signals. The complication of the setup is therefore high and the setup is fragile and uncomfortable for the patient. The result is that this kind of study is mostly done at a hospital or specialized sleep clinics and for one night only. PSG ambulatory sleep studies performed at people's homes are less common due to these complications; even with the obvious benefits of measuring the patient in his conventional environment and resulting reduction of cost.

Electrocardiography (ECG) is an important tool for sleep diagnostics and gives valuable indicators due to its connection with sleep-related parameters, blood pressure and arousals. Heart-rate-variability (HRV) and pulse-transit-time (PTT) are examples of useful parameters that provide significant indications on the sleep/wake pattern of a subject. If setup of more complicated sensors, like ECG electrodes, could be performed by a patient or assistant at home, this would increase the quality of the studies, save work and make multiple-night sleep recordings possible.

Capacitive Electrodes

The general idea of capacitive electrodes is to use a different way of measuring up the electrophysiological signals, such as for example ECG signals. When using conventional electrodes, the aim is to provide a good signal connection by minimizing the electronic resistance between the electrode lead and the patient body fluids. The idea behind electro-capacitive electrodes is however instead of basing the signal conductivity on resistance, to form a maximum capacitance connection for the same purpose. As the conductivity of capacitance is variable with frequency this does however require that the amplifier input resistance must be extremely high, for the signal in the band-width of interest to be detected.

The simplest form of a capacitor between the body and the electrode lead would be a metallic plate, where the surface has been coated with a thin layer of isolating material. By pressing the plate towards the body a parallel plate capacitor has been formed. Any electronic activity in the body will cause electronic field to be formed over the isolating material of the plate. By measuring the field or the voltage caused by the field, the electronic body signals can be measured the same way as when conventional electrodes are being used, but without being in direct galvanic contact with the body.

Such capacitive electrode can be generally described by equation (1):

$$C = \varepsilon * A/d \tag{1}$$

where $\varepsilon$ is a constant, A is the area of the surface of the electrode, d is the effective insulating distance (the distance between the electrode surface and the bodily fluids constituting the inherent "circuit" of the body).

This kind of electrode was first described in the late 60s and patented in 1970. (P. Richardson and A. Lopez, Jr., "Electrocardiographic and Bioelectric Capacitive Electrode," U.S. Pat. No. 3,500,823, granted 17 Mar. 1970). The capacitive electrode disclosed by Richardson and Lopez comprises a round disk, 1.5 in diameter, and 0.125 in thick, with an insulating coating on the surface facing the skin of a subject. Typical characteristics of such electrode include a resistance of greater than 4 G$\Omega$ (Gigaohms) at 50 V and a capacitance of 5000 pF (picofarad) at 30 Hz.

The general problems of such capacitive electrode include that the signal amplifier used must have an impedance value on par with the high impedance of the electrode and preferably substantially higher, so as not to lose too much of the signal potential, before the signal is measured. A second more complicated problem is that the impedance of the electrode is variable, depending on the distance 'd', between the electrode surface and the bodily fluids, which distance will change as a result of bodily movements (e.g. breathing). This second problem has been generally addressed by having a very thin insulating layer on the electrode to increase the capacitance, and by strapping the electrode rigidly to the body so as to minimize the fluctuations in the distance d and thus fluctuations in C.

SUMMARY

The present disclosure provides in a first aspect a system for measuring biometric signals, the system comprising at least two electrodes wherein at least one of which is a flexible capacitive electrode. Preferably, the second electrode is as well a capacitive electrode having a flexible structure. The system can suitably comprise at least two flexible conducting electrodes that can be placed on or around the body of a subject, wherein voltage is measured between the two electrodes.

The present disclosure utilises new circuit design and measurement configuration, such that the measured capacitive signal can provide a well resolved and accurate measurement of biosignals, e.g. ECG measurements, decoupling the effects of the high variability of the capacitance of the circuit.

The at least two electrodes may suitably be arranged as flexible belts, preferably these are elastically deformable, such that they can be fit snugly on the torso of a subject.

In one embodiment, the system comprises two electrodes configured to be placed around the thorax and abdomen respectively, of a subject. In such embodiment, the system can suitably be configured to simultaneously determine the respiratory effort of the patient. Preferably, in such system the electrodes form flexible belts for determining respiratory effort based on Respiratory Inductive Plethysmography (RIP) technology.

It follows that the electrodes as described herein can in one embodiment form at least two belts for determining respiratory effort as a simultaneous measurement with a capacitance measurement for determining electrocardiography (ECG) signals. Preferably the electrodes form belts for determining respiratory effort based on Respiratory Inductive Plethysmography (RIP) technology, but other means for measuring respiratory effort are as well encompassed by the concepts of the present disclosure, as described in more detail herein.

Another aspect of the present disclosure provides a method for measuring biosignals from a subject, comprising:

placing at least one flexible capacitive electrode on the subject, connected in a circuit,
measuring the voltage between said at least one flexible capacitive electrode and a reference point and transmitting a signal to a high-input impedance amplifier, and
processing the received signal and outputting a useful biosignal.

The method can suitably be performed with a system such as described herein.

In a preferred embodiment the method further comprises generating an added current signal with a signal generator connected to said circuit, said added signal having a frequency substantially removed from the frequency of the biosignal of interest,
measuring the voltage signal of the frequency component corresponding to the added current signal to thereby determine fluctuations in the overall impedance and fluctuations in the capacitance of the circuit, and
correcting for fluctuations in the capacitance to obtain a corrected voltage signal representing the measured biosignal and outputting said signal.

DETAILED DESCRIPTION

Figure 1:
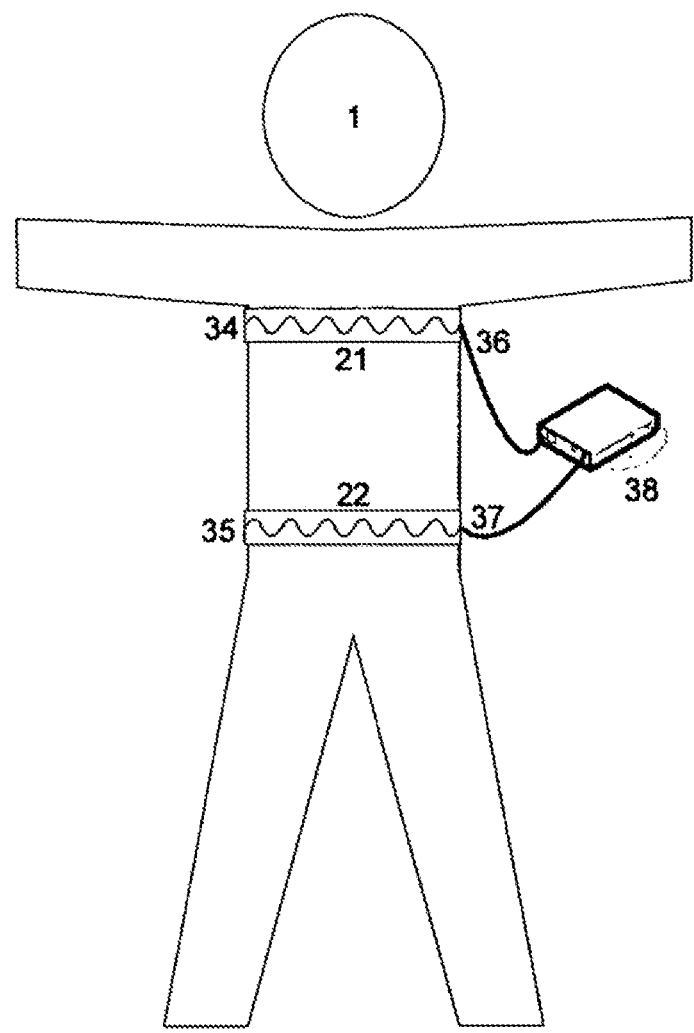
FIG. 1 illustrates a system of the present disclosure according to a first embodiment with electrodes in the form of conductive belts wrapped around the thorax 34 and abdomen 35 of a person 1.

Prior art electrodes for formation of capacitive electrodes do have in common that they are based on a rigid plate that is pressed toward some place of the body where the desired signal is located.

The use of flexible and/or elastic electrodes, as in the present disclosure, provide critical benefits, and certain challenges as well, which however are solved by the present disclosure.

The present disclosure provides a different concept of using capacitive electrodes for measuring biosignals. The present disclosure is based on using a flexible electrode, such as in particular a belt, a cord, a sheet or the like. The term "flexible" as used in this context indicates an electrode with a structure which can have substantially varying capacitance during use, i.e. the capacitor formed between the electrode and the body of a subject may and generally will vary when in use on a live subject, and no particular measures need be taken to eliminate or minimize such variations, as in prior art systems based on rigid capacitive electrodes.

Preferably, the electrode is flexibly adjustable such that it can be fit snugly on a subject, but without having to restrict normal movements of the subject. Thus, systems and electrodes of the present disclosure can be used for sleep measurements where the subject can rest and sleep comfortably, while the electrodes are mounted and the system in operation.

In certain embodiments, the capacitive electrodes can be formed by one or more of the following:

Weaving, sewing or knitting of conductive material into flexible and/or elastic material,
Lamination of conductive material between layers of flexible and/or elastic material,
Gluing of conductive material onto the surface of flexible and/or elastic material,
Coating a flexible and/or elastic material with conductive film The belts electrodes can in some embodiments be described by the term "textile-like", which in this context is meant to describe any type of fabric, including woven, sewn or knitted fabric but the electrodes may also be of plastic type or from rubber or a rubber-like material, or any mixtures or combination of the above.

The present disclosure encompasses systems with at least one flexible capacitive electrode, and a reference point, which can be a conventional electrode mounted on the subject but is in preferred embodiments described herein a second capacitive electrode.

It is however within the scope of the present disclosure to use alternative electrode setup, based on the same principles described herein. For example, a setup with one electrode mounted on the front of the torso of a subject and an opposite electrode on the back of the subject, can as well be used for capacitive measurements as described herein.

As mentioned above, one of the great challenges when using flexible electrodes is that movements of the electrodes result in capacitance changes that directly affect the measured signal and this results in disturbances and errors. The voltage over a capacitor is inversely modulated by the change in capacitance. It is very difficult to keep the capacitance constant of the capacitor formed between a capacitive electrode and the body, as movements do cause disturbances to occur that can be deleterious to the measurement. This is solved by the present disclosure by measuring the absolute or differential value of electrode-capacitance, where the form of the disturbance can be calculated and cancelled from the signal. This can be suitably done by applying to the circuit a known added signal current with a frequency preferably above the band-width of interest (e.g. sufficiently above to be separable from the biosignal of interest which is to be measured). Modern signal processing technology allows very sharp cut-off thresholds for frequency filters (hi- or low-pass filters); depending on the biosignal of interest, the added signal current can have a frequency of about 50 Hz or higher, but more preferably about 100 Hz or higher, such as about 200 Hz or higher, such as about 400 Hz or higher or 500 Hz higher, or a value even higher than those. Modern signal processing technology also allows a known form signal to be subtracted from the original signal, even if the bandwidth of the two overlaps. This method is practical where the band of interest is wide.

The signal transmits through the circuit across the overall capacitor formed in the circuit (the known capacitance and the body-capacitance) and therefore the absolute value of the body capacitance can be calculated by comparing the applied signal with the measured signal. As the voltage over the capacitor can have a DC component that is unknown, it is not enough to know the capacitance change to calculate the strength of the disturbance, only the form is known. The strength can however be calculated by comparing the capacity signal with the measured signal, using signal processing methods and convolution. With the form and strength of the disturbance known, the signal can then be cleaned up by the use of subtraction of the disturbance from the signal. The total impedance of a capacitor in a circuit can be described by equation (2):

$$Z=1/(j(2 \times PI \times f \times C)) \quad (2)$$

By separating a frequency component which comprises the frequency of the added signal current, which is sufficiently removed from the biosignal of interest to allow for effective separation of the two, the total impedance can be calculated by determining the voltage of said frequency component.

FIG. 1 shows a general setup of two electrodes in the form of conductive belts wrapped around the body of a human subject 1, comprising a thorax belt 34 and abdomen belt 35. The signals are transmitted by thorax lead 36 and abdomen lead 37 to a high input impedance measurement device 38.

Figure 2:
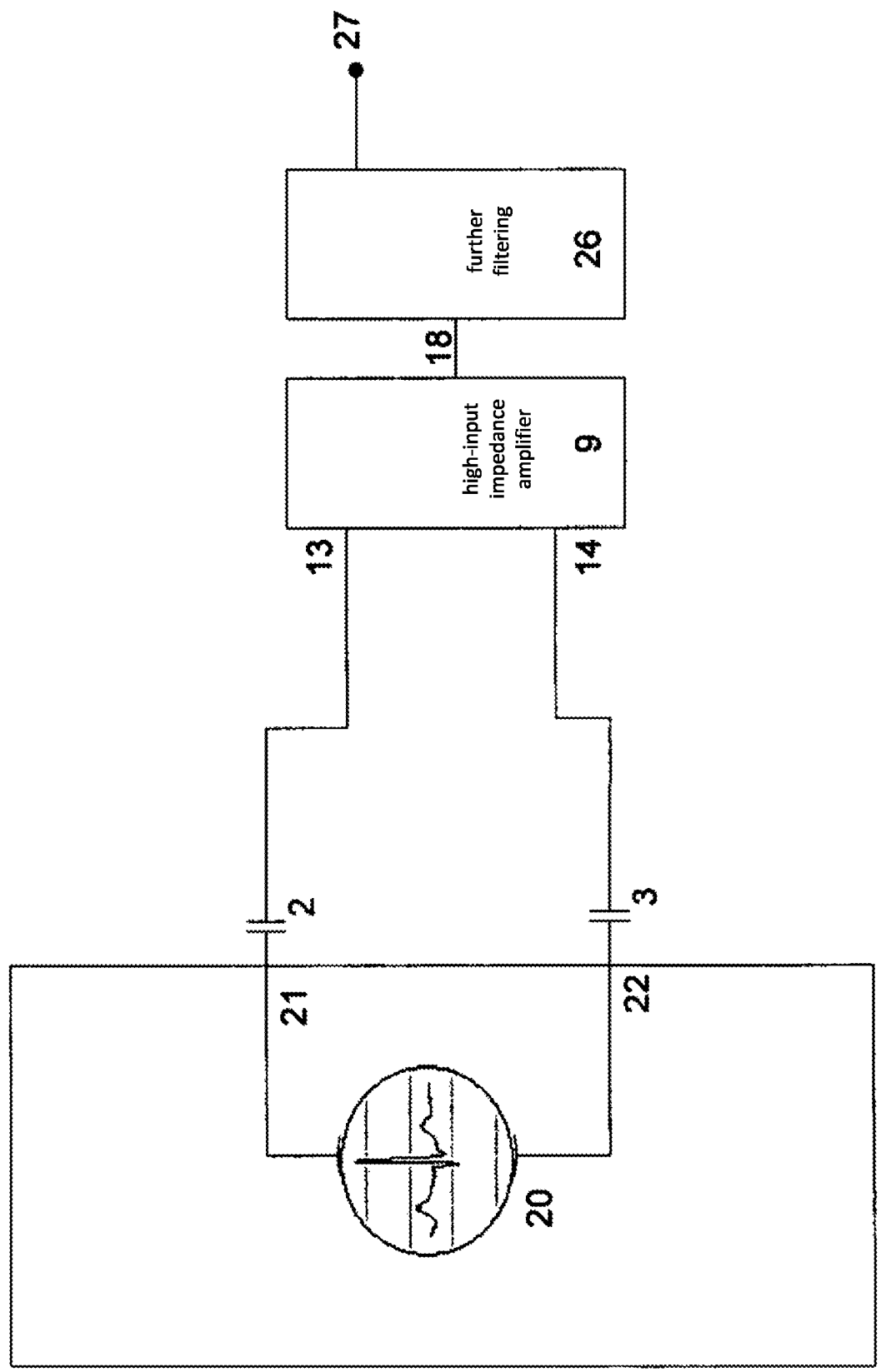
FIG. 2 shows schematically equivalent circuitry of a basic system of another embodiment.

FIG. 2 shows the electrically equivalent circuitry of the system in FIG. 1. The subject 1 generates an electrophysiological signal 20. The thorax belt is positioned at a point/height 21 above the heart but the abdomen belt at a point/height 22 below the heart. The thorax belt forms a capacitor 2 with the body at point 21 and the abdomen belt forms a capacitor 3 with the body at abdomen point 22. The signal picked up is transmitted through the belts and leads to the inputs 13, 14 of a high-input impedance amplifier 9 that delivers a low-impedance signal 18 to further filtering at 26. The signal output 27 is then delivered for further signal processing.

Figure 3:
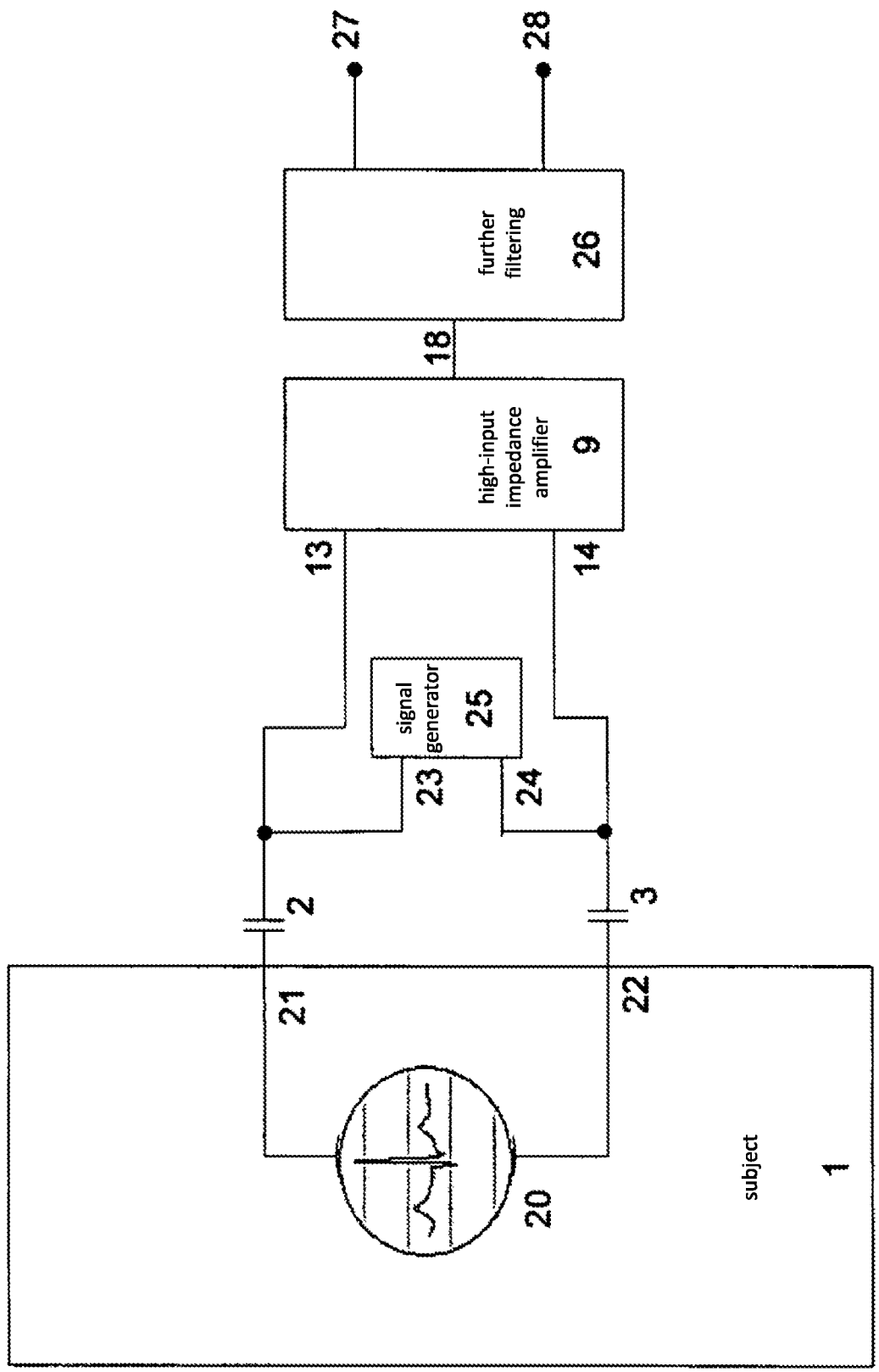
FIG. 3 shows a schematic circuit as in FIG. 2, but with added high-output impedance function generator.

FIG. 3 shows the electrically equivalent circuitry where a signal generator 25 has been added to the circuit of FIG. 2. The high-output impedance function generator 25 generates a differential alternative measurement current between outputs 23 and 24. This current flows through the body 1 over the body-belt capacitors 2 and 3. The frequency of said added current is above the frequency of the biosignal 20 of interest. The signal generated by the current is amplified by the high-input impedance amplifier 9. The output signal of the amplifier 18 contains the sum of both the signal of interest 20 and the signal generated by the generator 25. In this case the signal processing at 26 splits the output signal in two parts, one part 27 containing the signal of interest, and the other part 28 containing information relating to the added signal generated by the generator 25.

Double Use of Respiratory Effort Belts in General

Any conductive belt that is placed on the body forms a capacitor with the body. As long as the impedance between two or more such electrode belts is kept sufficiently high and the body-capacitance is sufficiently high, the electro-physiological voltage signal between the belts can be measured. Due to the strength of electric signals arising from the heart, ECG measurements are especially suitable for of measurement with the embodiments of the present disclosure. It will be appreciated that in the described embodiments, flexible sensors that have already been placed on the body can include respiratory effort belts.

In a preferred embodiment, the thorax belt is placed around the body at a point 21 above the heart-position, while the abdomen belt is placed at a point 22 below the heart-position. The electronic field caused by the heart, that is the ECG signal, therefore appears between the belts.

In the respiratory effort belts, either the sensors' impedance is modulated with the respiratory movement or the circuit produces an electronic signal internally that is modulated with the respiratory movement. The sensors are therefore configured with two or more leads from each belt. By measuring either the belt impedance or the signal generated by the belt, the respiratory movement is measured.

By measuring the potential between the belts, the ECG can be derived without the use of any conventional electrode and without applying additional sensor. This adds a valuable signal while it keeps the complexity of the setup low and at the level such that measurements can be performed by non-medical personnel.

The double use of the respiratory effort belts is therefore based on measuring the differential or impedance signal for a single belt for the respiratory effort, but to measure the potential signal between two or more belts for the electrophysiological signal.

Figure 4:
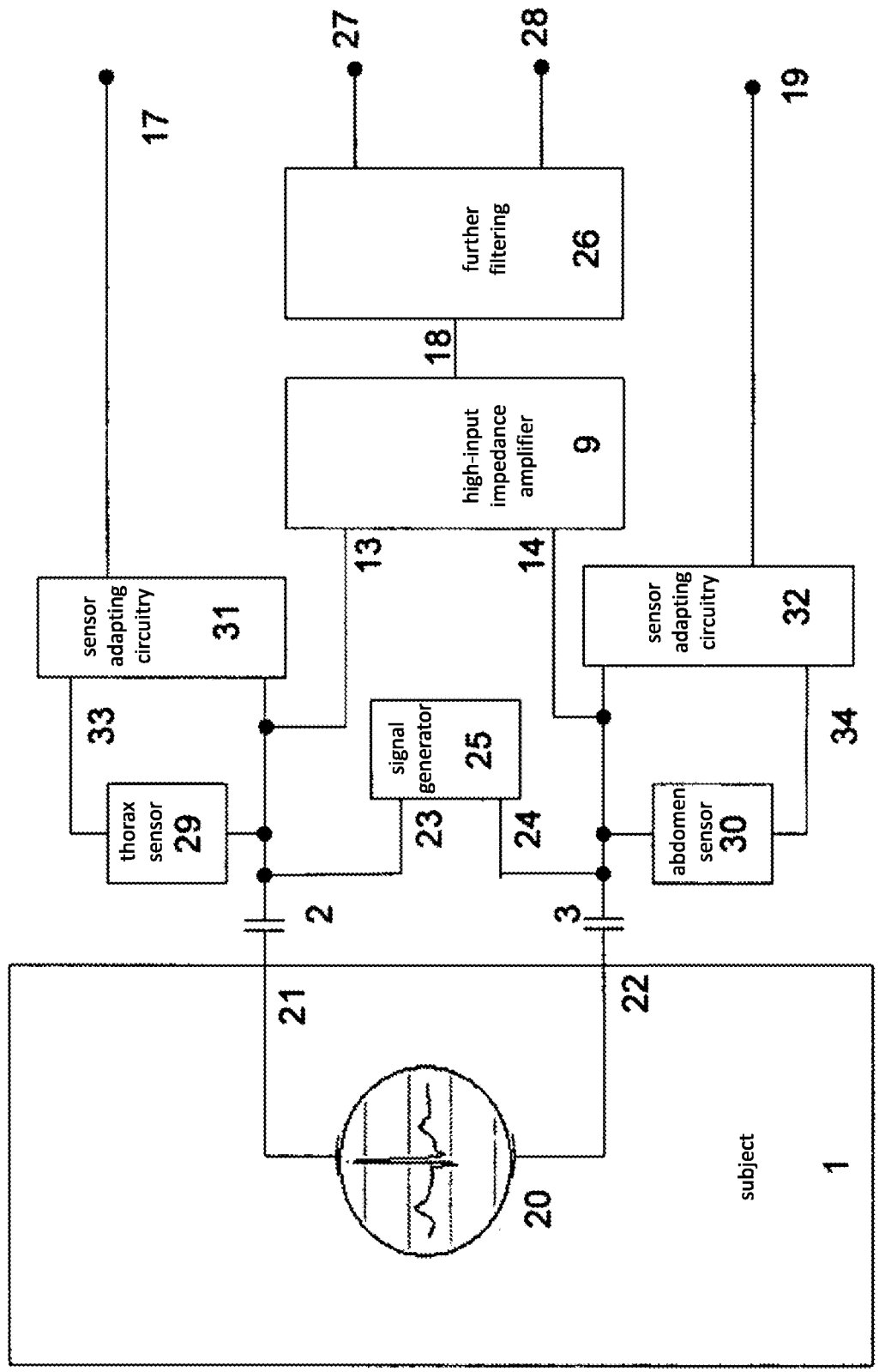
FIG. 4 shows a setup for measuring both ECG, capacitively, and respiratory effort.

FIG. 4 illustrates this setup in more detail. Thorax sensor 29 and abdomen sensor 30 form stray-capacitance 2 and 3 with the body 1 to which the electrodes are applied. The thorax sensor is connected to its sensors adapting circuitry 31 in points 33 and 13. The abdomen sensor is connected to its sensor adapting circuitry 32 in points 64 and 14. The signals generated by the sensors appear on the signal outputs 17 and 19 while the ECG signal appears as before on its signal output 27. As before, this circuit can be used with or without the capacitance measurement unit 25 that delivers additionally information on the capacitance changes and thereby movement artifacts on signal output 28.

Double Use of RIP Belts

The "gold standard" for respiratory belts used in sleep diagnostics are based on the so called RIP technology or Respiratory Inductive Plethysmography. The technology is based on the fact that the inductance of a wire loop is directly proportional to the area of the loop. If a wire is placed tightly around a body of a person, the inductance measured is therefore directly proportional to the cross-sectional area of the body inside the loop, which area changes as the person breathes in and out. By measuring the inductance of one loop around the thorax and one around the abdomen, a good measure of the changes of lung volume can be derived and based on that, the respiratory effort can be calculated.

The wire used to form the inductance does however also forms a capacitor with the body. As normally for RIP measurements only the inductance of the belt is measured, the signal is not affected by this capacitance. By measuring the voltage signal between the belts, the ECG can however be derived.

As the capacitance formed between the belts and the body is very low, in the range of hundreds of pF, the isolation between the belts on the device side must be very high. ECG bandwidth is starting around 1 Hz, which requires the input impedance of the device to be above about 1 GOhm. Accordingly, the term "high-input impedance amplifier" as used herein indicates an amplifier with sufficiently high impedance that it becomes substantially larger than the impedance of the capacitor formed in the circuit. Thus, in a high-input impedance amplifier, the impedance should be at least as high as the capacitance of the circuit, and preferably at least 5 times higher and more preferably at least 10 times higher and yet more preferably at least 20 times higher. For measuring ECG signals, which have an inherent voltage of around 10 mV and lie in the frequency spectrum in the range of about 0.5 to 200 Hz, the impedance of suitable capacitive electrodes is in the range of about 1 GOhm or higher, and consequently, a high-input impedance amplifier in such embodiment preferably has an impedance of about 1 GOhm or higher, such as for example 5 GOhm or higher, including 10 GOhm or higher.

Conventional RIP devices do however require a very low output impedance to drive the measurement current for the inductance measurement. Typically this current is in the frequency range of around and above 100 kHz.

Figure 5:
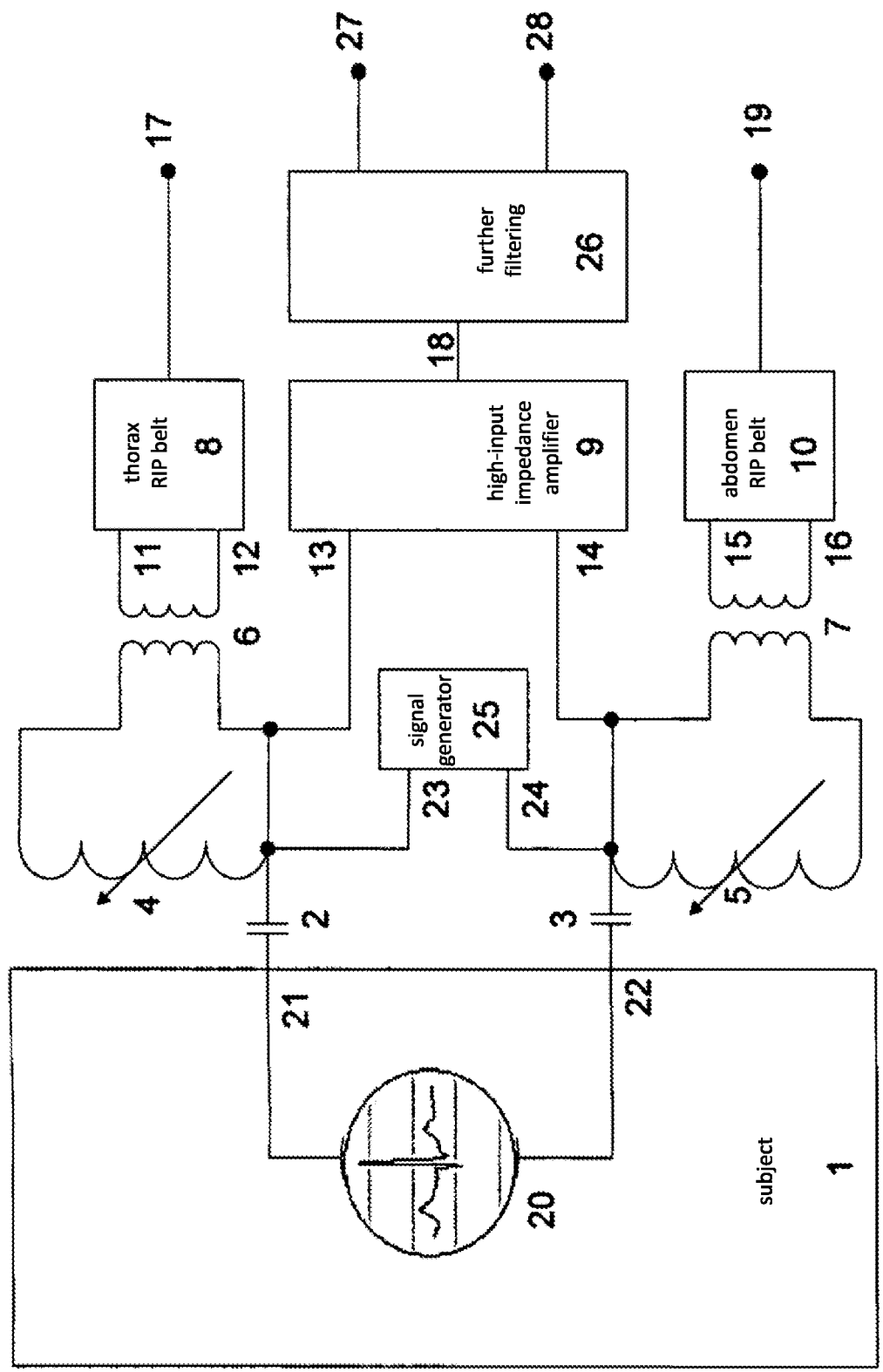
FIG. 5 shows the inductance of a thorax belt and an abdomen belt, being modulated by the respiratory movements of a patient.

In FIG. 5, the inductance of the thorax belt 4 and the abdomen belt 5 are modulated by the respiratory movements of the patient 1. Additionally the wire of the belts forms a stray-capacitance 2 and 3 to the patient. A resonance module is formed for both the thorax 8 and the abdomen 10 RIP belts that deliver signals 17 and 19, containing the respiratory movement signals in one form or the other. The resonance frequency in 8 and 10 is most often measured in tens or hundreds of kHz. A practical problem using the RIP function in combination with capacitive electrode function is that while the electrodes require high input impedance, the impedance of the resonance circuitry is required to be low. To avoid this problem a thorax transformer 6 and abdomen transformers 7 have been added, providing the required high common mode impedance for the electrode but still allowing a low impedance excitation of the RIP belts. As before, this circuit can be used with or without the capacitance measurement unit 25 that delivers additionally information on the capacitance changes and thereby movement artifacts on signal output 28.

Double Use of Piezo Belts

Instead of using RIP belts with a conductor for measuring respiratory effort through inductance measurements, it is also known in the prior art to measure respiratory effort by using elastic belts that pull a piezo-crystal or film at one or more points. The respiratory effort (breathing movements) stretch the elastic belt which this modulates the strain on the piezo material and forms an electronic signal proportional to the movement. If a belt in such application is partially or fully made of conductive materials, they would form a capacitance with the body. Accordingly, in an embodiment of the present disclosure the system comprises one or more piezo-element integrated with one or more elastic belts that comprise electrodes for the primary biosignal measurement, which is suitably an ECG measurement, and the one or more piezo-elements are used for measuring respiratory effort. FIG. 4 illustrates the equivalent electronic circuit for this application, where the sensors 29 and 30 represent piezo elements and the capacitors 2 and 3 are the capacitors formed between the patient 1 and the sensors/conductors within the belts.

Double Use of Resistive Polymer Belts

These types of respiratory effort belts are made from an elastic material that has one or more threads made of elastic polymer that has been blended to give it some conductance. The length and diameter of the polymer threads are modulated with the stretching of the belt, and therefore the belt electrical resistance is also modulated. In this case, either the polymers themselves can be used to form the capacitance with the body, the belt may be coated with conducting material giving the capacitance, or the belt can contain additional conductive materials that form the capacitance. The present disclosure encompasses embodiments with capacitive electrodes for the primary biosignal measurements of the disclosure and where the system comprises resistive polymer sensors for measuring respiratory effort. In this configuration, the resistive polymer sensors need not lie around the patient but can be, e.g., integrated in sheets that when placed appropriately on a subject stretch as the subject breathes.

FIG. 4 describes an equivalent electronic circuit for this application, where the sensors 29 and 30 represent the resistive elements and the capacitors 2 and 3 the capacitors formed between a subject 1 and the sensors/belts. In this case the sensors adapting circuitries 31 and 32 provide the required common mode isolation, to keep the input resistance of the circuitry sufficiently high.

Capacitive electrodes do introduce new sources of disturbances as they are in a weaker connection with the electrical signal than conventional skin electrodes. The high impedance through the capacitance makes them more sensitive for pickup of stray-electro-magnetic fields and as described above, the capacitance is not fixed but is modulated by any movement between the body and the electrode and a modulation of the capacitance is directly coupled into a disturbance artifact directly proportional to the voltage over the capacitor. A method for measuring online the capacitance and using the measured capacitance signal to optimise filtering of those disturbances has already been described above.

Increasing the Body-Electrode Capacitance.

For the flexible electrodes described above, and especially for double use of the respiratory effort belts as capacitive electrodes, the capacitance can be increased and thereby the strength of the measured signal can be increased.

For RIP belts the wire used is normally highly conductive but thin. As the capacitance between the body and the belt is based on the surface area of the conductor across the corresponding area of the body, this capacitance can be suitably increased by increasing this area when using such belts in the present disclosure.

One way of doing this in the present disclosure is to use more than one conductor in parallel in the belt manufacturing and thereby increasing the capacitance area. Two wires in parallel would basically double the belt-body capacitance, etc.

Another way is to give the normally non-conductive RIP-belt base-material some conductance by blending them with conductive material (i.e., mixing in conductive material, soaking in conducting material, or by any other means). The now conductive base material in this way forms capacitance both with the body and with the wire in the RIP belts and thereby increases the overall body-belt capacitance. As the input resistance of the amplifier is very high, the electrical resistance of the belt material does not necessarily need to be very low for this to significantly increase the overall body-belt capacitance.

In another embodiment, the base material is made conductive by having some or all of the belt threads made of conductive materials. This could for example be tinsel-wire, resistive polymer or alike. These conductors would have both capacitive coupling with the RIP-wire and the body and thereby increase the overall body-belt capacitance.

Windowed Pulse Detection.

For many medical applications, it is not necessary to measure all the details of an ECG signal. Often, only the timing of the ECG pulse is of interest and therefore only the R-component of the ECG is of interest in such situations. The R-component is a spike that is significantly larger in amplitude than other components of the ECG signal, so it can be detected from signals with relatively low signal-to-noise ratio (SNR). In the case of recording with capacitive electrodes, it can be the case that the SNR is significantly lower compared with conventional skin-electrodes. The timing of the R-component is of special interest in sleep diagnostics, as it is both used for heart-rate measurements, heart-rate variability measurements and calculations of pulse transit time. If the signal has a low signal-to-noise ratio, the capability of positioning the R-component can be significantly improved by limiting the time-window where it may have appeared. In sleep diagnostics the time-window of the R-component can be limited in two ways.

If a pulse oxymeter signal is recorded simultaneously, every heartbeat results in a pulse in the oxymeter plethysmogram, few milliseconds later. This information can be used to limit the time-window to the last few milliseconds before the oxymeter pulse.

If the movements of the thorax are being monitored using respiratory effort belts, the motoric function of the heart-beat is picked up along with the respiratory signals. As this function is always a result the electrical function few milliseconds before, the position of the motoric pulse can be used to reduce the search area for the electrical pulse.

The present disclosure is however not limited to such embodiments as just mentioned; in other useful embodiments, more heart signals are measured, comprised in normal ECG measurements, such as but not limited to the QRS complex, the P wave, the PR interval, the ST segment, the CT segments, etc. These signals are useful for diagnosing various heart conditions, such as cardiac arrhythmias, conduction abnormalities, ventricular hypertrophy, myocardial infarction, electrolyte derangements, and other disease states.

The Use of Flexible Electrodes for Other Signals than ECG.

In general it is more comfortable to put a belt on rather than to put on a conventional electrode with direct conductive contact with the skin. The belts can therefore also be used instead of electrodes without sharing any function with RIP technology. This may for example be practical to measure EMG signals on limbs using two straps instead of electrode, EMG between neck and thorax used for example for sleep/wake determination or to form a simple-to-put-on EEG/EOG assembly of electrodes, by introducing conductive wire into an elastic cap covering head areas of interest.

The invention claimed is:

1. A system for measuring biometric signals that include an electrophysiological signal from the body and a signal for determining respiratory effort based on respiratory inductive plethysmography (RIP), the system comprising:

at least two electrodes that form belts configured to be placed at least partially around the torso of a subject for determining respiratory effort, at least one of which belt comprises a capacitive electrode with a flexible structure, wherein a conductor within said at least one belt is insulated, such that the conductor does not come in direct contact with skin of a subject when the belt is placed on said subject, the system having a circuit for measuring the voltage between said at least two electrodes, and wherein the system is configured to determine electrocardiography (ECG) signals or electromyography (EMG) signals through the measurement of the voltage between said at least two electrodes and to determine the respiratory effort of the subject.

2. A system for measuring biometric signals, the system comprising:

a first electrode that forms at least a portion of a first belt configured to be placed at least partially around a torso of a subject;

a second electrode that forms at least a portion of a second belt configured to be placed at least partially around the torso of the subject; and a circuit configured to measure a voltage between the first electrode and the second electrode, wherein the first electrode and the second electrode are arranged to determine a respiratory effort of the subject, and the first electrode or the second electrode includes a capacitive electrode with a flexible structure including an insulated conductor, the insulated conductor being insulated such that the conductor does not come in direct contact with skin of the subject when the first electrode or the second electrode is placed on the subject, and wherein the system is configured to determine an electromyography (EMG) signal through the measurement of the voltage between the first electrode and the second electrode and to determine the respiratory effort of the subject.

3. The system of claim 2, wherein the first electrode and the second electrode each respectively include a flexible elastically deformable capacitive electrode.

4. The system of claim 2, wherein said circuit comprises a high-input impedance amplifier.

5. A system for measuring biometric signals, the system comprising:

a first electrode that forms at least a portion of a first belt configured to be placed at least partially around a torso of a subject;

a second electrode that forms at least a portion of a second belt configured to be placed at least partially around the torso of the subject; and a circuit configured to measure a voltage between the first electrode and the second electrode, wherein the first electrode and the second electrode are arranged to determine a respiratory effort of the subject, and the first electrode or the second electrode includes a capacitive electrode with a flexible structure including an insulated conductor, the insulated conductor being insulated such that the conductor does not come in direct contact with skin of the subject when the first electrode or the second electrode is placed on the subject, and wherein the system is configured to determine an electrocardiography (ECG) signal through the measurement of the voltage between the first electrode and the second electrode and to determine the respiratory effort of the subject.

6. The system of claim 5, wherein the first electrode and the second electrode each respectively include a flexible elastically deformable capacitive electrode.

7. The system of claim 5, wherein the system is configured to determine the respiratory effort of the subject based on respiratory inductive plethysmography (RIP).

8. The system of claim 7, wherein a belt-to-belt insulation is achieved by using electronic transformers for a RIP signal.

9. The system of claim 5, further comprising a processor configured to correct for fluctuations in the capacitance in the circuit.

10. The system of claim 9, wherein said circuit comprises a signal generator configured to generate an added known form current signal to a biosignal to form a voltage signal, the biosignal including a signal obtained from the first electrode or the second electrode, or the measurement of the voltage between the first electrode and the second electrode, wherein the voltage signal includes a sum of the added known form current signal and the biosignal; and wherein the circuit further comprises a voltage measurer configured to measure the voltage signal including the sum of the added known form current signal and the biosignal; and a signal splitter configured to split the measured signal into components of the biosignal and the added known form current signal.

11. The system of claim 10, wherein said added known form current signal has a frequency of about 50 Hz or higher.

12. The system of claim 5, wherein said circuit comprises a high-input impedance amplifier.

13. A method for measuring biometric signals from a subject using the system according to claim 5, the method comprising:

placing the first electrode on the subject, the first electrode being connected in the circuit;

measuring a signal based on the voltage between the first electrode and a reference point at the second electrode, both of the first electrode and the second electrode forming induction belts;

inputting the signal to a high-input impedance amplifier;

processing the signal to determine the ECG signal;

outputting the ECG signal; and determining the respiratory effort of the subject.

14. The method of claim 13, wherein the first electrode includes the capacitive electrode with the flexible structure.

15. The method of claim 14, wherein the second electrode includes another capacitive electrode with a flexible structure.

16. The method of claim 15, further comprising:

generating a known added current signal with a signal generator connected to the circuit, said known added current signal having a shape separable from a biosignal of interest, the biosignal of interest including:

a signal obtained from the first electrode or the second electrode, or the measurement of the voltage between the first electrode and the second electrode;

measuring a voltage signal of the sum of the known added current signal and the biosignal of interest;

determining fluctuations in an overall impedance and fluctuations in a capacitance of the circuit;

correcting for the fluctuations in the capacitance of the circuit to obtain a corrected voltage signal representing the biosignal of interest; and outputting said corrected voltage signal as the biosignal of interest.

17. The method of claim 16, wherein the known added current signal has a frequency of above about 50 Hz.

18. The method of claim 13, wherein said biometric signals include a signal for determining the respiratory effort based on respiratory inductive plethysmography (RIP).

* * * * *